United States Patent

Gilad et al.

Patent Number: 6,114,392
Date of Patent: Sep. 5, 2000

[54] AGMATINE, AND POLYAMINOGUANIDINE-BOUND HETEROCYCLIC COMPOUNDS FOR NEUROTRAUMA AND NEURODEGENERATIVE DISEASES

[76] Inventors: Gad M. Gilad; Varda H. Gilad, both of 21 Rahel, 53482 Givatayim, Israel

[21] Appl. No.: 08/632,835

[22] Filed: Apr. 16, 1996

Related U.S. Application Data

[62] Division of application No. 08/430,086, Apr. 27, 1995, abandoned.

[51] Int. Cl.[7] ...... A61K 31/155; A61K 31/132; A61K 31/15; A61K 31/133
[52] U.S. Cl. ...... 514/634; 514/579; 514/612; 514/632; 514/633; 514/636; 514/645; 514/659; 514/660; 514/661; 514/662; 564/116; 564/225; 564/227; 564/229; 564/230; 564/236; 564/237; 564/243; 564/248; 564/270; 564/453; 564/458; 564/459; 564/460; 564/461
[58] Field of Search ...... 564/116, 227, 564/229, 230, 236, 237, 225, 243, 453, 460; 514/612, 632, 633, 634, 631, 636, 645, 659, 660

[56] References Cited

U.S. PATENT DOCUMENTS

| | | | |
|---|---|---|---|
| 4,837,218 | 6/1989 | Olney | 514/646 |
| 5,190,976 | 3/1993 | Weber et al. | 514/634 |
| 5,262,568 | 11/1993 | Weber et al. | 564/238 |

*Primary Examiner*—Peter O'Sullivan
*Attorney, Agent, or Firm*—Mark M. Friedman

[57] ABSTRACT

The invention relates to the use of agmatine, in the treatment of acute neurotrauma (such as stroke) and degenerative disorders of the central and peripheral nervous system (such as dementia).

The invention further provides novel compounds of general formula I (which are quinuclidine derivatives), formula II (which are norbornane derivatives), formula III (which are adamantane derivatives), and formula IV (which are phenothiazine derivatives):

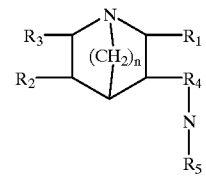

Formula I

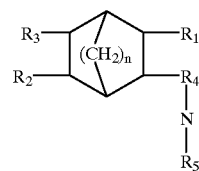

Formula II

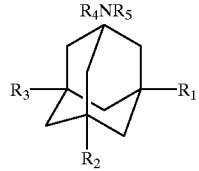

Formula III

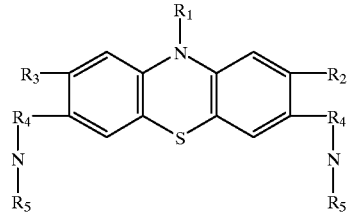

Formula IV wherein $R_1$, $R_2$ and $R_3$ are each independently hydrogen, hydroxy, substituted or unsubstituted $C_{1-4}$ alkyl, substituted or unsubstituted $C_{1-4}$ alkoxy, halogeno, amino, phenyl, or $R_4NR_5$; $R_4$ and $R_5$ are each independently hydrogen, or $(CH_2)n-[NH(CH_2)x]y-NHR_6$, or $(CH_2)n-[NH(CH_2)x]y-NH-NHR_6$, or $(CH_2)n-[NH(CH_2)x]y-(NR_7=)CNHR_6$, or $(CH_2)n-[NH(CH_2)x]y-NH(NR_7=)CNHR_6$ wherein n is from 0–5, y is from 0–5 and each x is independently from 1–5; $R_6$, and $R_7$ are each independently hydrogen, hydroxy, substituted or unsubstituted $C_{1-4}$ alkyl, substituted or unsubstituted $C_{1-4}$ alkoxy, or halogeno; and pharmaceutically acceptable salts and optically active isomers thereof.

15 Claims, No Drawings

AGMATINE, AND POLYAMINOGUANIDINE-BOUND HETEROCYCLIC COMPOUNDS FOR NEUROTRAUMA AND NEURODEGENERATIVE DISEASES

This is a division of U.S. patent application 08/430,086, filed Apr. 27, 1995, now abandoned.

FIELD AND BACKGROUND OF THE INVENTION

The present invention relates to agmatine, a naturally occurring compound, and to novel derivatives thereof, and to hydrazine and polyamine derivatives, medicating compositions containing them, and the use thereof, especially in the treatment of acute neurotrauma (such as stroke) and degenerative disorders of the central and peripheral nervous system (such as dementia).

Agmatine. This naturally occurring compound is utilized mainly as a precursor for polyamine synthesis. Agmatine synthesis by decarboxylation of arginine, is catalyzed by the enzyme arginine decarboxylase (ADC) which is present in bacteria, plants and some invertebrates, but not in higher animals (Tabor C W & Tabor H. Ann Rev Biochem 53:749, 1984). Agmatine metabolism in animals is largely unknown.

Agmatine has been reported to possess a wide range of activities related to functions of the nervous system. Such activities include interaction with membrane receptors, such as nicotine, NMDA and intracellular imidazoline receptors. It can serve as ADP-ribose acceptor and thereby inhibit ADP-ribosylation of proteins. Agmatine may prevent collagen cross-linking in diabetes and aging, and may regulate epithelial cell growth in wound healing. Agmatine produces insulin-like effects in animals. Agmatine may serve as a precursor for biosynthesis of polyamines, compounds that possess a wide range of activities both within and external to the central nervous system (e.g., modulation of postsynaptic receptors, such as N-methyl-D-aspartate (NMDA), nicotinic and benzodiazepine receptors, antiplatelet, antiinflammatory and anticoagulant activities); The effect of the polyamines spermine, spermidine and putrescine in protecting against ischemia-induced nerve cell death in gerbils were described by Gilad G. M. et al. [Life Sci (1989) 44:1963–1969; Exp Neurol (1991) 111:349–355; Biochem Pharmacol (1992) 44:401–407]. Various molecules containing an aliphatic polyaminoguanidine chain have been synthesized and screened in a variety of animal models of central nervous system disorders. Many of these compounds have been based on toxins extracted from spiders (e.g. *A. aperta* and Argiopelabata) and the wasp triangulum. These compounds comprise a long poly(aminoalkane) chain (related to polyamines) linked to an aromatic or heterocyclic group through a carbonyl group. Disadvantages associated with using the polyamines and derivatives, relate to various toxic side effects that would hinder these compounds from proceeding to clinical use.

Importantly, agmatine not only proved to be relatively non-toxic, but at some concentrations it rather accelerates cell proliferation.

New findings on the activity of agmatine in laboratory models of neurotrauma, constituting part of the basis for this invention, will be described herein.

A disadvantage associated with using agmatine itself for chronic central nervous system disorders relates to transport through biological membranes.

SUMMARY OF THE INVENTION

The present invention seeks to provide agmatine itself, $(NH_2)$—$(CH_2)_4$—$NH(NH=)CNH_2$ [Merck Index, 11th ed., Merck & Co., Inc., Rahway (1989) pp. 31], and derivatives of agmatine and other guanidines, hydrazine, polyamines and related compounds, herein referred to as "polyaminoguanidine derivatives", that improve or retain the activity of the parent compounds, and display fewer undesirable side effects.

Accordingly, the present investigation relates to compounds of several general formulae, depending on the heterocyclic congener:

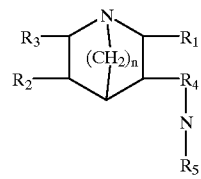

Formula I

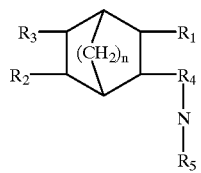

Formula II

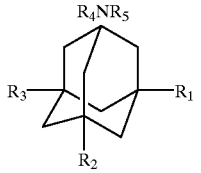

Formula III

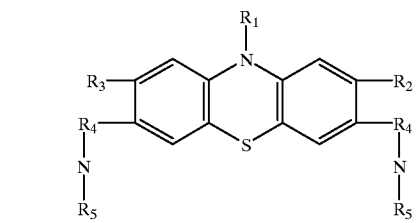

Formula IV wherein $R_1$, $R_2$ and $R_3$ are each independently hydrogen, hydroxy, substituted or unsubstituted $C_{1-4}$ alkyl, substituted or unsubstituted $C_{1-4}$ alkoxy, halogeno, amino, phenyl, or $R_4NR_5$; $R_4$ and $R_5$ are each independently hydrogen, or $(CH_2)n$—$[NH(CH_2)x]y$—$NHR_6$, or $(CH_2)n$—$[NH(CH_2)x]$ $y$—$NH$—$NHR_6$, or $(CH_2)n$—$[NH(CH_2)x]y$—$(NR_7=)$ $CNHR_6$, or $(CH_2)n$—$[NH(CH_2)x]y$—$NH(NR_7=)CNHR_6$ wherein n is from 0–5, y is from 0–5 and x is from 1–5; $R_6$, and $R_7$ are each independently hydrogen, hydroxy, substituted or unsubstituted $C_{1-4}$ alkyl, substituted or unsubstituted $C_{1-4}$ alkoxy, or halogeno; and pharmaceutically acceptable salts and optically active isomers thereof.

The compounds of formula I are quinuclidine or azabicyclo[2,2,1]heptan derivatives, those of formula II are norbornane derivatives, those of formula III are adamantane derivatives, and those of formula IV are phenothiazine derivatives of agmatine and other guanidines, hydrazines, polyamines and related compounds, and simple isomers thereof. Many of the compounds of the general formulae I–V are optically active, the present invention further relates to the purified optically active isomers.

DESCRIPTION OF THE PREFERRED EMBODIMENTS

Within the general formula I it is generally preferred that n is 1 or 2, that is the compounds are amino derivatives of quinuclidine or azabicyclo[2,2,1]heptan. Within the general formulae II it is generally preferred that n is 1, that is the compounds are amino derivatives of norbornane. Within the general formulae I–IV it is generally preferred that R1, $R_2$ and $R_3$ are each independently hydrogen, hydroxy, substituted or unsubstituted $C_{1-4}$ alkyl, substituted or unsubstituted $C_{1-4}$ alkoxy, halogeno, amino, phenyl or $R_4NR_5$.

It is further preferred that $R_4$ and $R_5$ are each independently hydrogen, or $(CH_2)n—[NH(CH_2)x]y—NHR_6$, or $(CH_2)n—[NH(CH_2)x]y—NH—NHR_6$, or $(CH_2)n—[NH(CH_2)x]y—(NR_7=)CNHR_6$, or $(CH_2)n—[NH(CH_2)x]y—NH(NR_7=)CNHR_6$, wherein n is from 0–5, y is from 0–5 and each x is independently from 1–5; $R_6$, and $R_7$ are each independently hydrogen, hydroxy, substituted or unsubstituted $C_{1-4}$ alkyl, substituted or unsubstituted $C_{1-4}$ alkoxy, or halogeno; and pharmaceutically acceptable salts and optically active isomers thereof.

In such formulae embodiments, the group $R_4NR_5$ may be in the "R" or "S" configuration. Preferably, it is in the "R" configuration.

The present invention also provides for the pharmaceutical composition compromising a therapeutically effective amount of the above-listed compounds, including agmatine, and a pharmaceutically acceptable carrier.

This invention provides for the pharmaceutical composition wherein the pharmaceutically acceptable carrier is a solid and the pharmaceutical composition is a tablet. In one embodiment, the therapeutically effective amount is from about 1 mg to about 1000 mg. In a more specific embodiment, the therapeutically effective amount is from about 10 mg to about 100 mg.

In another embodiment of the pharmaceutical composition, the pharmaceutically acceptable carrier is a liquid and the pharmaceutical composition is an ingestible solution. In a specific embodiment, the therapeutically effective amount is from about 1 mg/ml to about 1000 mg/ml. In a more specific embodiment, the therapeutically effective amount is from about 10 mg/ml to about 100 mg/ml.

In an embodiment of the pharmaceutical composition, the carrier is a gel and the pharmaceutical composition is a suppository.

This invention further provides a method for treating acute neurological traumatic disorder or neurotrauma in a subject comprising administering to the subject a therapeutically effective amount of agmatine, or of a compound of the formulae I–IV.

The subject invention further provides a method of treating a subject afflicted with a neurodegenerative disease, such as Alzheimer's disease, Parkinson's disease, amyotrophic lateral sclerosis, etc. This comprises administering to the subject an amount of agmatine, or of a compound of general formulae I–IV, or the pharmaceutically acceptable salt thereof of the subject invention effective to treat the neurodegenerative disease in the subject.

The subject invention further provides a method of treating a subject afflicted with a neurotoxic injury which comprises administering to the subject an amount of agmatine, or of a compound of general formulae I–IV, or the pharmaceutically acceptable salt thereof of the subject invention effective to treat the neurotoxic injury in the subject.

The subject invention further provides a method of treating a subject afflicted with brain ischemia which comprises administering to the subject an amount of a compound of agmatine, or of a general formulae I–IV, or the pharmaceutically acceptable salt thereof of the subject invention effective to treat brain ischemia in the subject.

The subject invention further provides a method of treating a subject afflicted with a head trauma injury which comprises administering to the subject an amount of agmatine, or of a compound of general formulae I–IV, or the pharmaceutically acceptable salt thereof of the subject invention effective to treat the head trauma injury in the subject.

The subject invention further provides a method of treating a subject afflicted with a spinal cord traumatic injury which compromises administering to the subject an amount of agmatine, or of a compound of general formulae I–IV, or the pharmaceutically acceptable salt thereof of the subject invention effective to treat the spinal cord traumatic injury in the subject.

The subject invention further provides a method of preventing nerve damage in a subject which comprises administering to the subject an amount of agmatine, or of a compound of general formulae I–IV, or the pharmaceutically acceptable salt thereof of the subject invention effective to prevent nerve damage in the subject.

The compounds of the present invention may also be of use in the following applications: 1) As immunosuppressants, as anti-neoplastic agents, anti-psoriatic agents, and in treatment of multiple sclerosis. 2) As anti-ulcerative agents. 3) As anti-protozoal agents.

The administering may comprise orally administering, rectally administering, or parenterally administering.

The terms acute neurological traumatic disorder or neurotrauma are used herein to refer to, and include clinical indications such as stroke, acute cranial injury, etc.

The novel compounds of the present invention, of formulae I–IV, may also be of use as wound healing agents when topically applied.

In another application, the compounds of the present invention may be effective as pest control (insecticide).

With reference to the accompanying schemes, the new polyaminoguanidine derivatives may be prepared from the parent 3-aminoquinuclidine, 3-aminonorbornane, 1-aminoadamantane, or 10-aminophenothiazine which are known, by reaction with compounds of the following formulae:

| Formula A | Formula B |
|---|---|
| X—(CH$_2$)n-NH—R$_8$R$_9$ | X—(CH$_2$)n-NH—NH—R$_8$R$_9$ |
| Formula C | Formula D |
| X—(CH$_2$)n-(NR$_7$=)CNHR$_6$ | X—(CH$_2$)n-NH(NR$_7$=)CNHR$_6$ |

Wherein: X is a suitable leaving group (such as halide, sulfonate ester, lower alkylthio or alkoxy radical) to enable N-alkylation by compounds of formulae A, B, or C; one or both of $R_8$ and $R_9$ are suitable amino protecting groups such as t-butyloxycarboxy (BOC), or together are phthaloyl; and $R_6$, $R_7$ and n are defined as previously.

The reaction between the heterocyclic compounds of formulae I–IV can be controlled to give the desired polyaminoguanidine derivatives and mixtures thereof that can be separated into pure compounds by methods known to those skilled in the art (chromatography, crystallization, etc.). The desired polyaminoguanidine derivatives may be isolated by removing the amine protective groups under appropriate conditions. For example, for symmetrical polyamine derivatives if $R_8$ is BOC, by treatment with hydrogen chloride in ether, and in the case of 3-aminoquinuclidine:

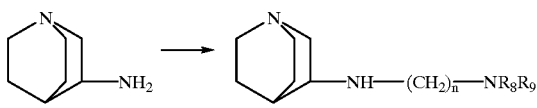

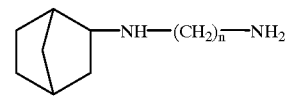

Unsymmetrical polyaminoguanidine derivatives may be prepared by reacting a second alternative compound of the formula A, B, or C with a partially protected diamine and the terminal protecting group may then be removed according to the above described method.

In general the polyaminoguanidine derivatives may be isolated as the salt of a suitable acid (e.g., hydrochloric, sulfuric, methansulfonic, etc.).

In another embodiment of this invention, compounds of this invention are prepared where the heterocyclic skeleton form an integral part of the polyaminoguanidine structure. For example, in this case the quinuclidine derivative may be 3,5 or 3,6-aminoquinuclidine, the norbornane derivative may be, 3,5 or 3,6-aminonorbornane, and the adamantane derivatives may be 1,3, 1,5, or 1,7-aminoadamantane. Each analogue may be isolated as the cis or trans isomer. The cis/trans mixture of the heterocyclic polyamino compounds may be resolved by any convenient means, preferably by conversion to the diacetyl amide and resolution by crystallization and/or chromatography. The isomerically pure diacetates may be hydrolyzed to the desired heterocyclic polyamino compounds under acidic conditions (preferably aqueous hydrochloric acid).

In a further embodiment of the invention, heterocyclic polyaminoguanidine compounds can alternatively be prepared directly from parent ketone derivatives of quinuclidine, norbornane, adamantane, or phenothiazine by reaction with mono-protected compounds of the following formulae:

| Formula A | Formula B |
|---|---|
| NH$_2$—(CH$_2$)n-NH—R$_2$R$_9$ | NH$_2$—(CH$_2$)n-NH—NH—R$_8$R$_9$ |
| Formula C | Formula D |
| NH$_2$—(CH$_2$)n-(NR$_7$=)CNHR$_6$ | NH$_2$—(CH$_2$)n-NH(NR$_7$=)CNHR$_6$ |

Wherein n, R$_6$, R$_7$, R$_8$ and R$_9$ are all defined as previously, to give the corresponding heterocyclic imines which may be reduced (preferably by sodium borohydride or by catalytic hydrogenation) followed by deprotection under conditions appropriate for the protecting group, preferably acid hydrolysis for the case where R$_8$ is BOC. In this case the product compound is isolated as a mixture of cis and trans isomers. For example, in the case of 2-norbornanone:

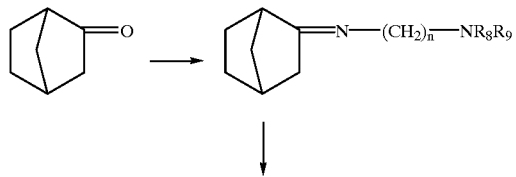

This invention will be better understood from the experimental details which follow. However, one skilled in the art will readily appreciate that the specific methods and results discussed are merely illustrative of the invention as described more fully in the claims which follow thereafter.

ILLUSTRATIVE EXAMPLES

Chemical Examples
1. Polyamine Derivatives of Phenothiazine
  a. 2-chloro-N-(4-aminobutyl)-10H-Phenothiazine-10-propanamine.2HCl (G102)

SYNTHETIC SCHEME

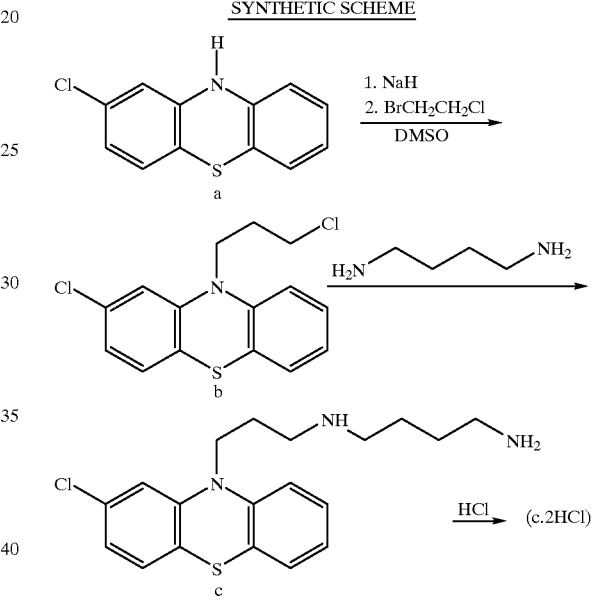

Synthesis of 2-chloro-N-(3-chloropropyl)phenothiazine (b): Sodium hydride (2.6 g, 60% in mineral oil, 60 mmol) was washed with hexane (2×15 ml), and dissolved in DMSO (30 ml), and added into a solution of 3-chloro-phenothiazine (6.5 g, 25 mmol) in DMSO (60 ml) at room temperature for a period of 5 min. The reaction mixture was then cannular-transferred into a solution of 1-bromo-3-chloropropane (15 g, 96 mmol) in DMSO (30 ml), while the temperature was kept at 25° C. After the addition was completed, the solution was stirred at room temperature for 1 h, and for an additional hour at 45–50° C., and then poured into ice water (300 ml). The mixture was then extracted with ethyl ether (3×300 ml). The extracts were washed with water, dried with magnesium sulfate, decolorized with active carbon, and concentrated to give a yellow oil which was purified by flash chromatography (ethyl acetate/hexane=5:95) to give compound b (5.0 g, 14.4 mmol, 58%). $^1$H NMR (300 MHz, CDC13) δ 7.15–6.80 (7H, m), 3.94(2H, t, J=8.2 Hz), 3.57 (2H, t, J=8.5 Hz), 2.15 (2H, m).

Synthesis of 2-chloro-N-(4-aminobutyl)-10H-phenothiazine-10-propanamine (c): 1,4-Diaminobutane (20 g, 225 mmol) and b (2.17 g, 6.3 mmol) were mixed at room temperature and then heated at 270° C. for 2 h. The excess diamine was then removed by distillation at reduced pressure. The solid residue was treated with concentrated ammonium hydroxide (20 ml), and extracted with ethyl acetate (3×80 ml). The extract was decolorized with active carbon and concentrated to give a crude oil which was purified by flash chromatography to give product c (2 g, 5.5 mmol), 88%). $^1$H NMR (300 Mhz, CDC13) δ 7.15–6.80 (7H, m), 3.86 (2H, m), 2.60 (6H, m), 1.85 (2H, m), 1.37 (4H, m), 1.10 (3H, s).

Synthesis of 2-chloro-N-(4-aminobutyl)-10H-phenothiazine-10-propanamine dihydrochloride (c.2HCl, G102): Compound (c) (1.5 g, 4.2 mmol) was dissolved in methanol (40 ml) and ether (130 ml), and then Hcl/ether (7 ml) was added. The precipitate was filtered and dried (70° C./0.2 mm Hg) for 10 min to give the product (1.5 g, 3.4 mmol, 83%); mp 238–239° C. (dec.); Anal for $C_{19}H_{26}Cl_3N_3S$, Calcd: C, 52.48; H, 6.03; N, 9.66. Found: C, 52.26; H, 6.13; N, 9.48.

b. 2-chloro-N-[3-(8-spermidinyl)]-10H-Phenothiazine-10-propanamine.3HCl (G103)

Synthesis of $N^1$, $N^2$, $N^3$-tricarbomethoxyspermidine. To a solution of spermidine (3.80 g, 26.7 mmol) in chloroform (40 ml) was added methyl chloroformate (12.5 ml), while cooling in an ice-water bath. Five min later, NaOH (9 g in 75 ml water) was added at room temperature, followed by 10 ml of methyl chloroformate, and the solution stirred for 3 h in ice-water bath. The chloroform layer was separated and the water phase extracted again with chloroform (250 ml). The combined chloroform extractions were dried with $MgSO_4$, and concentrated to give the product (8.40 g, 100%). $^1$H NMR (60 Mhz, CDCl$_3$) δ 5.50 (2H, s), 3.63 (9H, two s), 3.2 (8H, m), 1.6 (6H, m).

Synthesis of N-(4-aminobutyl)trimethylene urea (b). Barium hydroxide octahydrate (32.0 g) was added to a solution (250 ml) of tricarbomethoxy spermidine (4.40 g, 13.7 mmol) in water at 75° C. The reaction mixture was heated to 100° C. for 80 min. The barium salts were suction filtered and washed twice with water. The filtrate was extracted with chloroform (3×30 ml). The aqueous layer was concentrated and the residue combined with the filtered salts. The solids were boiled with absolute ethanol (100 ml), and after filtration and washing with more ethanol (4×20 ml), the filtrate was concentrated. The residue was re-dissolved in chloroform, dried with $MgSO_4$, and concentrated to give an oil which was purified by flash chromatography (MeOH:Et$_3$N=6:4) to give compound b (0.7 g, 4.08 mmol). $^1$H NMR (60 MHz, CDCl$_3$) δ 5.83 (1H, s), 3.20 (6H, m), 2.67 (2H, t, J=6.5 Hz), 1.87 (2H, m), 1.20–1.67 (6H, m).

Synthesis of 2-chloro-N-(3-chloropropyl)phenothiazine (a). Sodium hydride (2.6 g, 60% in mineral oil, 60 mmol) was washed with hexane (2 ×15 ml), dissolved in DMSO (30 ml), and added to a solution of 3-chloro-phenothiazine (6.5 g, 25 mmol) in DMSO (60 ml) at room temperature over a period of 5 min. The reaction mixture was then cannular-transferred into a solution of 1-bromo-3-chloropropane (15 g, 96 mmol) in DMSO (30 ml) at 25° C., and the solution was stirred first for 1 h at 25° C. and then for an additional hour at 45–50° C., and thereafter poured into ice-water (300 ml). This mixture was extracted with ethyl ether (3×300 ml), and the extracts washed with water, dried with magnesium sulfate, decolorized with active carbon, and was concentrated to give a yellow oil which was purified by flash chromatography (ethyl acetate/hexane=5:95) to give product

SYNTHETIC SCHEME

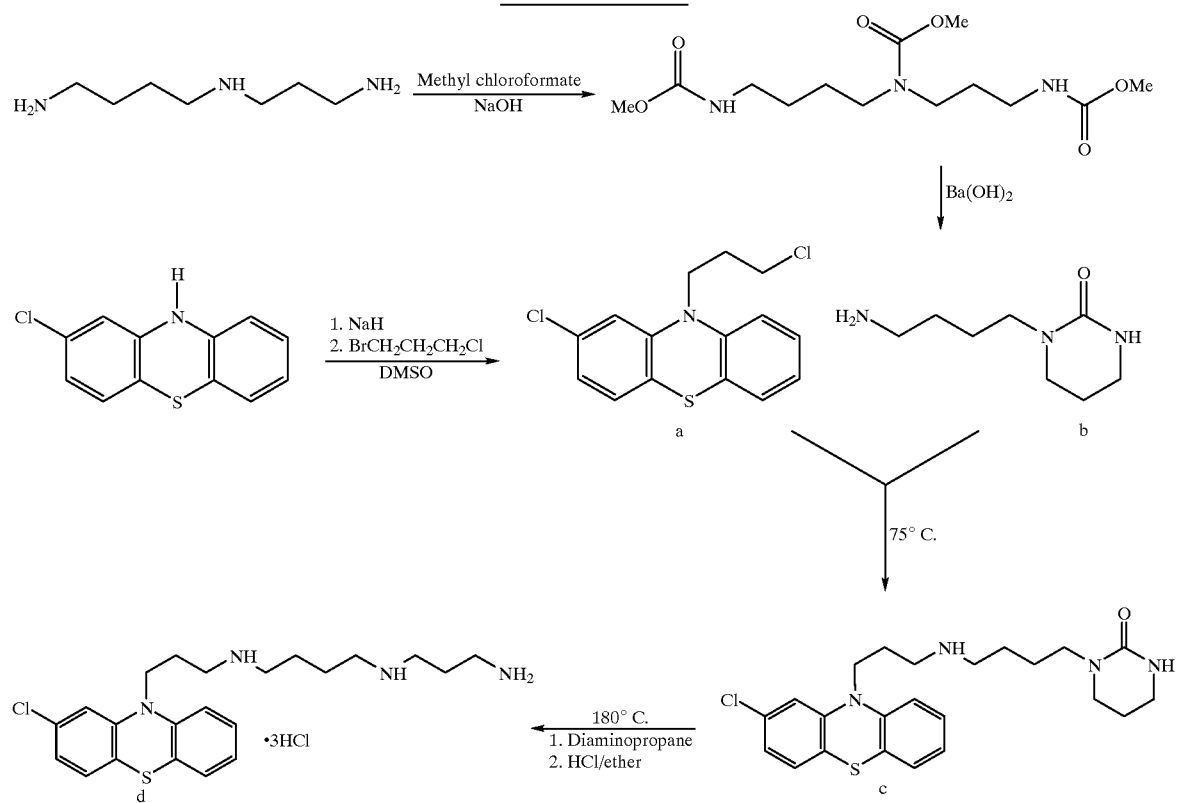

a (5.0 g, 14.4 mmol), 58%). $^1$H NMR (300 MHz, CDCl$_3$) δ 7.15–6.80 (7H, m), 3.94 (2H, t, J=8.2 Hz), 3.57 (2H, t, J=8.5 Hz), 2.15 (2H, m).

Synthesis of c. The cyclic urea (b) (0.38 g, 2.22 mmol) in chloroform was added to a solution of (a) (0.69 g, 2.22 mmol) in chloroform, and the reaction mixture concentrated to remove the solvent. The residue was heated to 70–80° C. overnight and the white solids dissolved in methanol (2 ml), concentrated again and the residue heated to 70–80° C. for additional 3 h. After addition of methanol (4 ml), the solution was passed through a column of silica gel using a mixture of ethyl acetate, triethylamine, and methanol (6:2:2) and yielded pure product (c) as a thick colorless oil (0.20 g, 0.45 mmol, 20%). $^1$H NMR (300 MHz, CDCl$_3$) δ 7.16–7.08 (2H, m), 7.00 (1H, d, J=6.0 Hz), 6.98–6.83 (4H, m), 5.02 (1H, s), 3.90 (2H, t, J=7.0 Hz), 3.30–3.17 (6H, m), 3.00 (1H, Broad s), 2.60 (4H, m), 1.95–1.82 (4H, m).

Synthesis of 2-chloro-N-[3-(spermidinylpropyl)]-10H-Phenothiazine trihydrochloride (d, G103). A mixture of 1,3-diaminopropane (3.00 ml) and (c) (0.30 g, 0.67 mmol) was heated at 170–180° C. fore 48 h in a sealed vial. Afterwards, the excess diamine was removed by distillation at reduced pressure (140° C./1 mmHg). The solid residue was dissolved in a solvent mixture (10 ml) of ethyl acetate, triethylamine, and methanol (6:2:2), and the solution passed through a short (5 cm) column of silica gel using first 200 ml of EtOH:MeOH:Et$_3$N (6:2:2) and then 600 ml of MeOH:Et$_3$N (6:4) as eluents. The white foam eluent, consisted of free base of (d) (0.20 g, 0.47 mmol), was dissolved in methanol (3 ml), added to a solution of Hcl in ether (5 ml), and concentrated to give a white solid which was re-crystallized in methanol to yield 85 mg of (d). mp 247° C. $^1$H NMR (300 MHz, CD,OD) δ 7.29–6.95 (7H, m), 4.09 (2H, t, J=8.0 Hz), 3.18–2.95 (10H, m), 2.22–2.05 (4H, m), 1.77 (4H, Broad s). M$^+$419, 100%. Anal for C$_{22}$H$_{34}$Cl$_4$N$_4$S (containing 7% 1,3-diaminopropane dihydrochloride): Calcd: C, 48.20; H, 6.61; N, 11.13. Found: C, 47.88; H, 6.57; N, 11.17.

BIOLOGICAL EXAMPLES

1. Cultures of Dissociated Neonatal Rat Cerebellum

The cerebellum is aseptically dissociated from 6 or 7-day old rat pups and placed in a 15 ml sterile plastic conical tube containing 3 ml of Dulbecco's modified Eagle's medium containing high glucose concentration (1 g/ml), 2 Mm (v/v) L-glutamine and an antibiotic mixture. The cerebella are then dissociated after 20–25 passages through a sterile 13 gauge, 10 cm long stainless steel needle attached to a 5 ml syringe with an inserted 45 micrometer pore nylon sieve. The dissociated cells are centrifuged at 200 g for 5 minutes. The supernatant is discarded and the cells resuspended in medium enriched with 15% (v/v) heat inactivated fetal calf serum. Cell viability is determined by the trypan blue exclusion test.

Cells are plated at a density of 200/mm$^2$ on poly-L-lysine coated surfaces which are prepared at least one hour in advance of plating by covering the surfaces (plastic Petri dishes or glass coverslips) with sterile distilled water solution containing 15 micrograms/ml poly-L-lysine, and washing in sterile water just prior to use. The plated cells are covered with enriched medium and incubated at 37° C. in an atmosphere of 5% CO$_2$ in air and 97% humidity. After three days in culture, the media is replaced with media containing the desired compound. Each compound is tested in duplicate and each experiment repeated at least once.

TABLE 1

Effect of compounds on nerve cell survival.

| Compound | Survival (μM) ≧20% | TD$_{50}$ (μM) |
| --- | --- | --- |
| Agmatine | 1–100 | 500 |
| Putrescine | — | 300 |
| Spermidine | 0.01 | 2 |
| Spermine | 0.01 | 2 |
| 2-Cl-phenothiazine | — | 5 |
| G102 - U-shaped dose-response curve: | | |
| descending curve: | — | 1 |
| ascending curve: | 300 | >1,000 |
| G103 | — | 2 |
| Quinuclidine | — | 100 |
| Mecamylamine | — | 500 |
| Adamantane | — | 1,000 |

Values, in μM, indicate the concentration, or a range of concentrations, which affected a 20% or more (≧) survival as compared to controls (100%). A lack of difference from control is indicated by a line (—).

1.A. Effect on Nerve Cell Survival and Toxicity in Culture

A concentration-dependent (dose-response) effect on nerve cell survival was determined for each compound at a concentration range of 0.001–5000 micromolar (μM). The compounds were added to 3-day-old cultures and the effect was examined 24 hours later.

Nerve cell survival was evaluated by phase contrast microscopy and trypan blue exclusion staining.

The results, summarized in Table 1, show the compound concentrations at which 20% or more cells survived (Survival) relative to controls, and at which 50% of the cells died (TD$_{50}$) when compared to controls. Control cultures were grown in enriched medium alone and represent 100% values.

1.B. Reversal of N-methyl-D-aspartate Induced Cell Death in Culture

Four groups were run in each set of experiments:
1. Control, consisting of cells grown in enriched media alone;
2. N-methyl-D-aspartate (NMDA, 1 Mm for 3 hours) as the cytotoxic challenge;
3. Test compound added after the NMDA challenge;
4. Positive control, spermine or spermidine (0.01 μM) after NMDA.

The number of surviving cells was examined 24 hours after the challenge. The results are shown in Table 2. Surviving cells in culture are measured relative to control (100%) as described above. Percent Protection is the cell survival for the test compound minus the NMDA effect. Thus, maximal protection is 100% minus the 30% NMDA effect, i.e. 70%. The Effective Protection value was calculated as the percent of the Percent Protection (X) divide by the maximal protection value (e.g. X×100/70).

TABLE 2

Nerve cell survival after NMDA neurotoxic challenge in cultures.

| Compound | [μM] | Surviving Cells in Culture (%) | Percent Protection | Effective Protection |
| --- | --- | --- | --- | --- |
| Control | 100 | | | |
| NMDA | 30 | | | |
| Maximal protection: | | | 70 | 100 |
| Agmatine | [10] | 65 | 35 | 50 |
| | [50] | 81 | 51 | 73 |

TABLE 2-continued

Nerve cell survival after NMDA neurotoxic challenge in cultures.

| Compound | [μM] | Surviving Cells in Culture (%) | Percent Protection | Effective Protection |
|---|---|---|---|---|
| Putrescine | [0.005] | 32 | 2 | 3 |
|  | [0.010] | 30 | 0 | 0 |
| Spermidine | [0.005] | 30 | 0 | 0 |
|  | [0.010] | 78 | 48 | 69 |
| Spermine | [0.005] | 25 | −5 | — |
|  | [0.010] | 68 | 38 | 54 |
| 2-Cl-pheno-thiazine | [10] | 45 | 15 | 21 |
|  | [50] | 62 | 32 | 46 |
| G102 | [1] | 70 | 40 | 57 |
|  | [50] | 35 | 5 | 7 |
|  | [250] | 95 | 65 | 93 |
| G103 | [0.01] | 55 | 25 | 36 |
|  | [0.10] | 32 | 2 | 3 |
|  | [1.00] | 20 | −10 | — |
| Quinuclidine | [1] | 35 | 5 | 7 |
|  | [10] | 40 | 10 | 14 |
| Mecamyl-amine | [25] | 67 | 37 | 53 |
| Adamantane | [10] | 43 | 13 | 19 |
|  | [50] | 50 | 20 | 29 |

2. Global Brain Ischemia In Gerbils

Male mongolian gerbils, aged 2.5–5 months, housed 4–8 in a cage, are supplied freely with food and water and maintained at 24° C. with a 12 hour day/night cycle. For surgery, the animals are anesthetized with halothane (1.5% in 100% $O_2$) and the common carotid arteries exposed bilaterally through a midline ventral neck incision. Each artery is clamped for 5 minutes with aneurysm clips to produce global brain ischemia. The anesthesia is discontinued upon clamping. After 5 minutes the clamps are removed and the wound closed with skin clips For treatment, the test compound or saline (0.9% NaCl, vehicle) are injected intraperitoneally (ip) in a volume of 50 microliters of solvent per 10 g body weight. The first injection is given 5 minutes after clamp removal, and thereafter daily for the next 2 post-operative days (total of 3 injections).

Four general groups, each of 4–8 animals were compare:
1. Control (sham, or unoperated and vehicle treated);
2. Ischemia, untreated or vehicle treated;
3. Ischemia, test compound treated, one sub-group per concentration tested;
4. Ischemia and pentobarbital (40 mg/kg) as positive control.

Analysis of neuronal damage was performed 14 days post-ischemia by counting pyramidal neurons throughout the CA1 layer of the anterior hippocampus in 4 micrometer thick (paraffin) coronal brain sections, stained with hematoxylin eosin. Values of cell numbers in the hippocampi of individual gerbils were expressed as percent of intact controls (control cell counts were 275±25 cells/mm$^2$).

The results are shown in the Table 3 below. Percent Protection values represent the fraction of hippocampi protected from ischemia in a group of animals treated with the stated dose of compound.

TABLE 3

Hippocampal neuroprotection after ischemia in gerbils.

| Test Compound [Dose in mg/kg] | (n) | Percent Intact Neurons | Percent Protection |
|---|---|---|---|
| Control | (10) | 100 |  |
| Ischemia | (10) | 0 |  |
| Pentobarbital | (8) |  | 87 |

TABLE 3-continued

Hippocampal neuroprotection after ischemia in gerbils.

| Test Compound [Dose in mg/kg] | (n) | Percent Intact Neurons | Percent Protection |
|---|---|---|---|
| Agmatine [10] | (5) |  | 20 |
| [50] | (5) |  | 50 |
| [100] | (5) |  | 75 |
| Putrescine [10] | (8) |  | 35 |
| Spermidine [10] | (8) |  | 50 |
| Spermine [10] | (8) |  | 65 |
| 2-Cl-pheno-thiazine [10] | (5) |  | 65 |
| G102 [1] | (5) |  | 40 |
| [5] | (5) |  | 70 |
| [10] | (10) | 70% toxic, all survivors were protected |  |
| G103 [0.01] | (10) |  | 42 |
| [0.10] | (8) |  | 55 |
| [0.50] | (5) | lethal |  |
| Quinuclidine [10] | (5) |  | 15 |
| Mecamyl-amine [10] | (5) |  | 40 |
| Adamantane [50] | (5) |  | 23 |

While the invention has been described with respect to a limited number of embodiments, it will be appreciated that many variations, modifications and other applications of the invention may be made.

What is claimed is:

1. Compounds of general formula II:

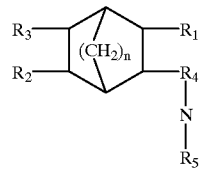

Formula II wherein:

n is 1 or 2;

$R_1$, $R_2$ and $R_3$ are each independently hydrogen, hydroxy, substituted or unsubstituted $C_{1-4}$ alkyl, substituted or unsubstituted $C_{1-4}$ alkoxy halogeno, amino, phenyl or $R_4NR_5$;

$R_4$ and $R_5$ are each independently, $(CH_2)_a$—[NH$(CH_2)_x$]$_y$—NHR$_6$, $(CH_2)_a$—[NH$(CH_2)_x$]$_y$—NH—NHR$_6$, $(CH_2)_a$—[NH$(CH_2)_x$]$_y$—(NR$_7$=)CNHR$_6$, or $(CH_2)_a$—[NH$(CH_2)_x$]$_y$—NH(NR$_7$=)CNHR$_6$, wherein a is 0–5, y is 1–5 and x is 1–5;

$R_6$ and $R_7$ are each independently hydrogen, hydroxy, substituted or unsubstituted $C_{1-4}$ alkyl, substituted or unsubstituted $C_{1-4}$ alkoxy, or halogeno;

and pharmaceutically acceptable salts and optically active isomers thereof.

2. The compounds of claim 1, wherein n is 1.

3. The compounds of claim 1, wherein $R_4NR_5$ is in the "R" configuration.

4. The compounds of claim 1, wherein the compounds are in the "cis" configuration.

5. The compounds of claim 1, wherein the compounds are in the "trans" configuration.

6. A pharmaceutical composition comprising a therapeutically effective amount of a compound of general formula II of claim 1 and a pharmaceutically acceptable carrier.

7. The pharmaceutical composition according to claim 6, wherein the pharmaceutically acceptable carrier is a solid and the pharmaceutical composition is a tablet.

8. The pharmaceutical composition according to claim 6, wherein the therapeutically effective amount is from about 1 mg to about 1000 mg.

9. The pharmaceutical composition according to claim 8, wherein the therapeutically effective amount is from about 10 mg to about 100 mg.

10. The pharmaceutical composition according to claim 6, wherein the pharmaceutically acceptable carrier is a liquid and the pharmaceutical composition is an injectable solution.

11. The pharmaceutical composition according to claim 10, wherein the therapeutically effective amount is from about 1 mg/ml to about 1000 mg/ml.

12. The pharmaceutical composition according to claim 1, wherein the therapeutically effective amount is from about 10 mg/ml to about 100 mg/ml.

13. The pharmaceutical composition according to claim 6, wherein the carrier is a gel and the pharmaceutical composition is a suppository.

14. The pharmaceutical composition according to claim 6, wherein the carrier is a topically acceptable vehicle.

15. The pharmaceutical composition according to claim 4, wherein the therapeutically effective amount is from about 0.005% to about 10% by weight of the active compound.

* * * * *